United States Patent [19]

Rudis et al.

[11] 4,137,776

[45] Feb. 6, 1979

[54] AUTOMATIC BASE GATE POSITIONING CIRCUIT

[75] Inventors: Robert P. Rudis, Burlington; Harry L. Ceccon, Boston, both of Mass.

[73] Assignee: The United States of America as represented by the Secretary of the Department of Transportation, Washington, D.C.

[21] Appl. No.: 903,518

[22] Filed: May 8, 1978

[51] Int. Cl.² ............................................. G01N 29/00
[52] U.S. Cl. ........................................ 73/611; 73/615
[58] Field of Search ................ 73/611, 615, 616, 636

[56] References Cited

U.S. PATENT DOCUMENTS

| | | | |
|---|---|---|---|
| 3,415,110 | 12/1968 | Cowan | 73/611 |
| 4,004,455 | 1/1977 | McKee et al. | 73/615 |
| 4,088,028 | 5/1978 | Hildebrandt | 73/611 |

*Primary Examiner*—Stephen A. Kreitman
*Attorney, Agent, or Firm*—Herbert E. Farmer; Harold P. Deeley, Jr.

[57] ABSTRACT

An automatic base gate positioning circuit for use in rail flaw detection is disclosed which includes the generation of a string of uniformly spaced pulses corresponding to known rail depth, correlating said pulses with sonic echoes averaging and storing the correlated signals and developing a signal representing the rail depth for comparison with an echo from the rail base.

4 Claims, 10 Drawing Figures

RAIL HEIGHT (INCHES)

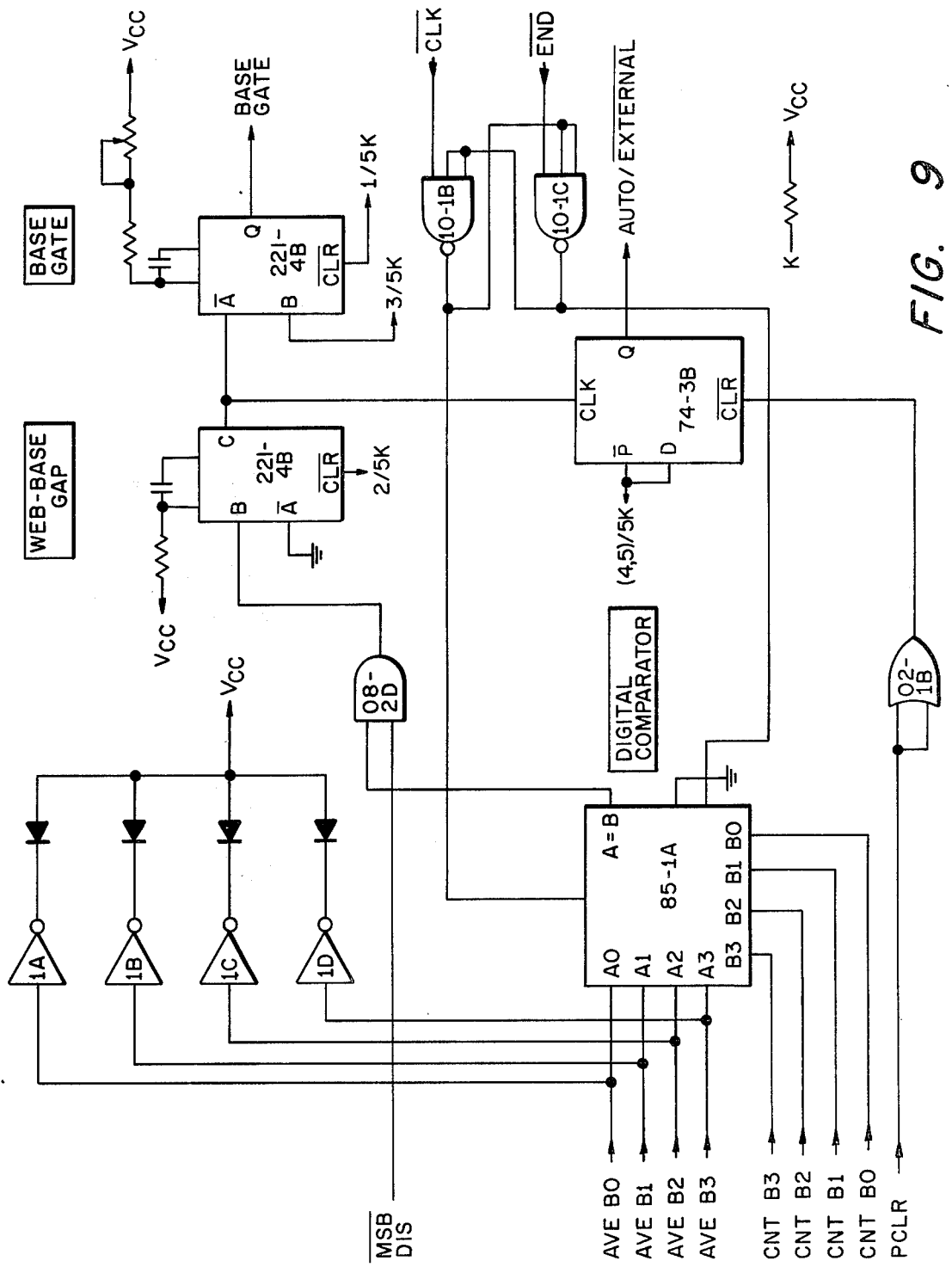

AUTOMATIC BASE GATE POSITIONING CIRCUIT

ORIGIN OF THE INVENTION

The invention described herein was made by employees of the United States Government and may be manufactured and used by, or for, the Government of the United States of America for governmental purposes without the payment of any royalties thereon or therefor.

BACKGROUND OF THE INVENTION

Ultrasonic signals are applied to the top of rails from moving vehicles. The ultrasonic energy travels from the top of the rail to its base. An echo indicates a flaw as the energy passes down through the rail. When the energy reaches the base a very strong echo is returned to the top of the rail for detection by the test apparatus which originally sent the ultrasonic signal into the top of the rail. In order to measure the precise moment that a return echo is received corresponding to the base of the rail, a time pulse is generated, corresponding to the generation of the ultrasonic signal and the return of the echo through the known depth of the rail. A strong echo at any precise moment on the time pulse indicates a flaw has occurred in the rail.

In summary then, with the depth of a rail known in advance timed pulses can be produced which correspond to the base echo. A loss of base echo at the precise time of the timing pulse predicts a strong evidence of a flaw or abnormality which requires very careful investigation of that rail in order to avoid a rail failure and its ultimate catastrophe.

The prior art utilizing this equipment has been very effective; however, rail thickness or depths vary considerably from rail bed to rail bed. When a rail change occurs, prior art ultrasonic generator and detector mechanisms must be recalibrated by adjusting the time pulse to correspond to the new rail thickness which requires stopping and adjusting the equipment.

The present invention completely automates ultrasonic testing of rails in that it provides an automatic method and means for measuring the thickness of the rail so that a base gate can be produced automatically corresponding to different rail thickness.

SUMMARY OF THE INVENTION

The invention is characterized by circuitry which produces a string of uniform pulses corresponding to the known variation in rail thicknesses wherein an echo should return. The timed pulses are processed according to the returned echo received in such manner that several samples of returned echoes are averaged and stored. The samples are large enough to produce a base gate signal which reflects the thickness of the rail. The processed base gate signal then is compared with incoming echoes as they would normally be processed in state-of-the-art apparatus; however, the base gate signal is predicated upon a large sample of echoes which control predetermined or pre-positioned timed pulses.

Therefore, an object of the present invention is to provide an automatic ultrasonic rail testing system which can accommodate a wide range of rail thicknesses automatically.

Another object of the present invention is to provide an ultrasonic rail testing device having the ability to generate its own base gate corresponding to the thickness of the rail with no a priori information with respect thereto.

Another object of the present invention is to provide base gate generating apparatus which samples a significant number of return echoes to process an average, reflecting the thickness of the rail for use in comparison with echoes in subsequent cycles.

Another object of the present invention is to provide base gate generating apparatus which samples a significant number of base echo returns so that returns from flaws or bolt hole patterns do not affect the rail height determination.

And still another object of the invention is to ensure that an automatically selected base gate is positioned such that the base echo return appears approximately in the center of the gate.

DESCRIPTION OF THE DRAWINGS

The foregoing objects and many of the attendant advantages of this invention will become more readily appreciated as the same become better understood by reference to the following detailed description when taken in conjunction with the accompanying drawings wherein:

FIG. 9 is the gating circuit.

Referring now to FIG. 1, shown is a video display. The display shows echo 7 and the gate 21 and 22. As it will be seen further, the gates correspond to the portion of the rail being examined. The gate 22 is the area of interest, and is the base gate to be concerned with. At the center of the base gate, the echo is shown to be returned, which is the sonic signal indicating that the rail has ended. Also, the web gate 21 which precedes the base gate and the flaw that would occur if the section of rail, known as the web, would indicate a reflection, or echo, at that time would be positioned immediately above it on the video display.

Referring now to FIG. 2, shown is the rail 2 together with the gates as they appear alongside the rail indicating the area of interest, or the reflection used in FIG. 1. The rail has three distinct sections: the head 5, the web 4, and the base 3. A fault can occur in any one of the sections of the rail. A very important examination is to know whether there is an echo from the base of the rail. If the base of the rail does not give a strong reflection back, an incomplete picture of the rail results. For example, it would not be known whether there was a change in rail thickness in the range from 5 to 8 inches, or whether there was a flaw in the head 5, or web 4 of the rail, or whether an impending catastrophe might readily occur unless that rail were changed.

The length of rail is approximately 39 feet per section. The sections may be bolted together so that when the sonic device pulses the rail near the junction of two sections of rail, the bolt holes will cause reflections in the web gate section. The sections may, alternatively, be welded together.

The rate of generation of sonic pulses in rail inspection is generally based on distance rather than time and, as a result independent of inspection vehicle speed. In addition, the distance driven rate is a preselected value upon which the circuit parameter of averaging cycle period is based. An averaging cycle period is a fixed preselected number of distance driven pulses used to determine the average position of a base echo. Table I shows rail length in inches corresponding to averaging cycle periods for different distance driven pulse rates. Preferred values of rail length are underlined. These values have been determined to be adequate samples to reflect the thickness of the rail and will discriminate, or exclude, spurious signals resulting from the bolt holes tying the rails together.

Table I.

|  |  | Pulses per Cycle | | | | |
|---|---|---|---|---|---|---|
|  |  | 32 | 64 | 128 | 256 | 512 |
|  | 3 | 10.67 | 21.33 | 42.67 | 85.33 | 170.67 |
|  | 4 | 8.0 | 16.0 | 32.0 | 64.0 | 128.0 |
|  | 5 | 6.4 | 12.8 | 25.6 | 51.2 | 102.4 |
| Pulse | 6 | 5.33 | 10.67 | 21.33 | 42.67 | 85.33 |
| Rate | 7 | 4.57 | 9.14 | 18.29 | 36.57 | 73.14 |
|  | 8 | 4.0 | 8.0 | 16.0 | 32.0 | 64.0 |
|  | 9 | 3.56 | 7.11 | 14.22 | 28.44 | 56.89 |
|  | 10 | 3.2 | 6.4 | 12.8 | 25.6 | 51.2 |

Length of rail in inches for various values of distance driven pulse rate vs. pulses per cycle.

Experience has shown that flaws are readily distinguishable with the given range of distance driven rates and the signature of a rail junction joining is readily distinguishable from a section of rail that has a flaw in it. The problem then is the varying thickness of rails. When a base gate signal is developed, representing the rail thickness, it has to be advanced in time in order to display it on the next cycle with the base return placed on the appropriate portion of the base gate pulse.

Figure 3:
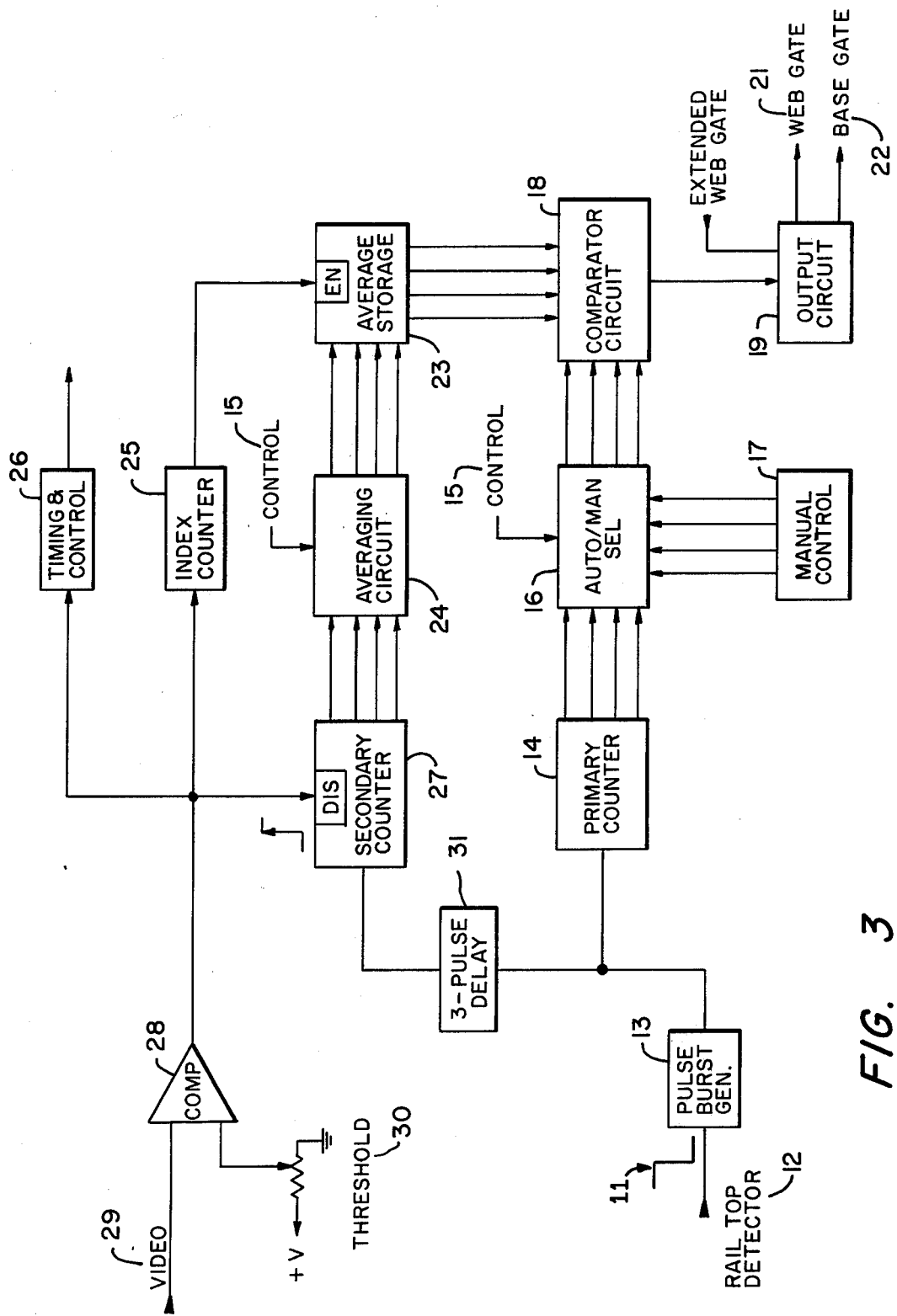
FIG. 3 is a block diagram of the present invention.

Referring to FIG. 3, pulse 11 triggers at the same time each ultrasonic bang is applied to the top of the rail. Thereafter and corresponding to the time it takes an ultrasonic signal to travel to the bottom of the rail and return from a thickness of approximately 4½ inches to the very largest anticipated rail thickness (8 inches), a pulse train is produced by the pulse burst generator 13. This pulse train is counted by a primary counter 14; and then through an automatic/manual selecting device 16 it is applied to a comparator circuit 18. The pulse train signal is also applied to a pulse delay apparatus 31. A secondary counter 27 also counts the pulses from burst generator 13 but does not start counting until the third pulse in the train is completed due to delay circuit 31. After the secondary counter 27 has been enabled, a signal from a comparator 28 processes an echo received (video 29) against a threshold determined by 30 and applies this signal which represents the echo from the base of the rail which disables the secondary counter 27. The secondary counter then applies its count to an averaging circuit 24. A control 15 permits the average to be transferred to a storage device 23. An index counter 25 is indexed once per ultrasonic bang by the return echoes which causes the accumulated secondary counter indications to be averaged over a prearranged number of ultrasonic bangs. The enabling circuit associated with average storage 23 applies the average to the comparator circuit 18. The primary count obtained after the next ultrasonic bang and average are now compared. When the two circuits match exactly the output circuit causes the web signal 21 to be terminated. A base gate 22 is also produced and positioned in time relative to the base echo such that the base echo will occur somewhere near the center of the base gate. The echo also triggers the timing and control device. The base gate 22 is then used to determine when the reflection should arrive with a given thickness of rail.

Figure 1:
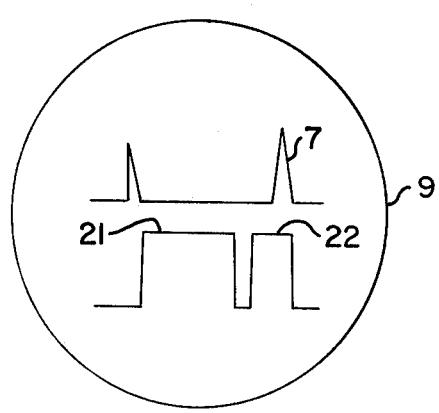
FIG. 1 is a video display of echoes and gate.
Figure 2:
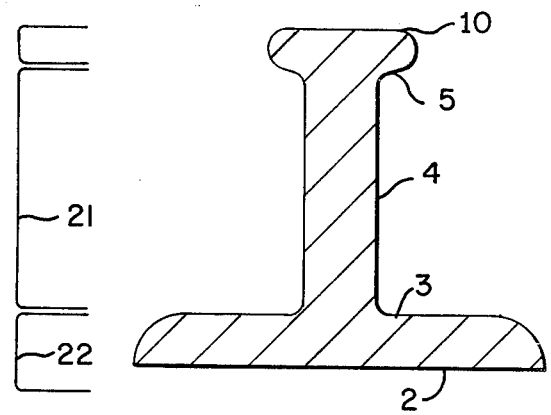
FIG. 2 is a rail with gates.
Figure 4:
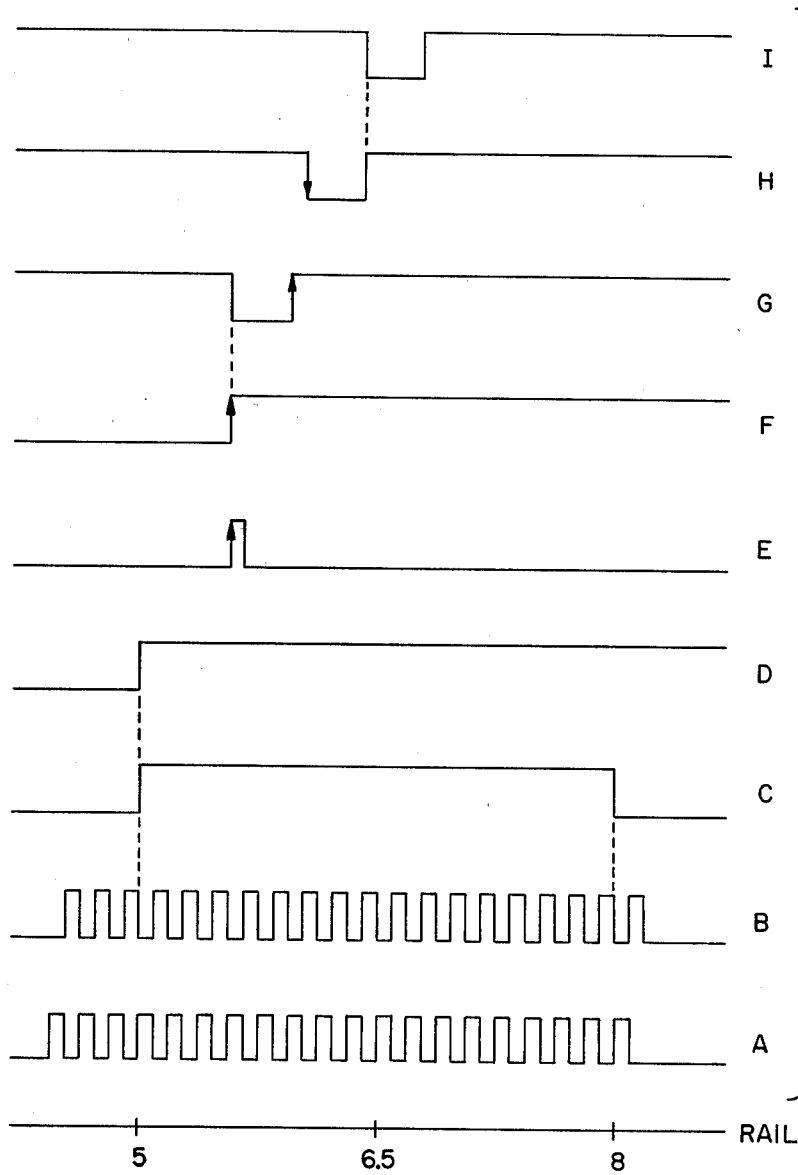
FIG. 4 is a wave diagram.

Referring now to FIG. 4, shown is the wave diagram and the position of the various pulses in the circuit. Referring to the string of pulses (4A), the clock, there are 20 pulses. The 20 pulses are positioned such that there are 16 pulse periods in the range of rail thicknesses, 5 to 8 inches. Each pulse is separated from one another, the same distance, and equal to the width of the given pulse. It will be observed below the clock pulses that the wave, or string of pulses, is a specific distance from the head on top of the rail.

FIG. 4B is the output of pulse burst generator 13; and delay circuit 31 permits the secondary counter 27 to commence counting by enabling circuit, pulse FIG. 4C. At that same time the secondary counter enabling signal FIG. 4D is also produced.

A typical digitized echo return FIG. 4E causes the pulse counter stop and storage FIG. 4F. As a result, the secondary counter is disabled and the secondary counter output transferred to storage to be added to previous secondary counter outputs. At the same time a pulse called xfer is generated (FIG. 4G), the trailing edge of which transfers the new sum to another storage element.

When the index counter 25 has reached its preselected count, average storage FIG. 4H is generated which causes the secondary counter average to be stored in another element. Immediately thereafter a clear signal FIG. 4I is generated which clears the circuit for the next cycle.

Figure 5:
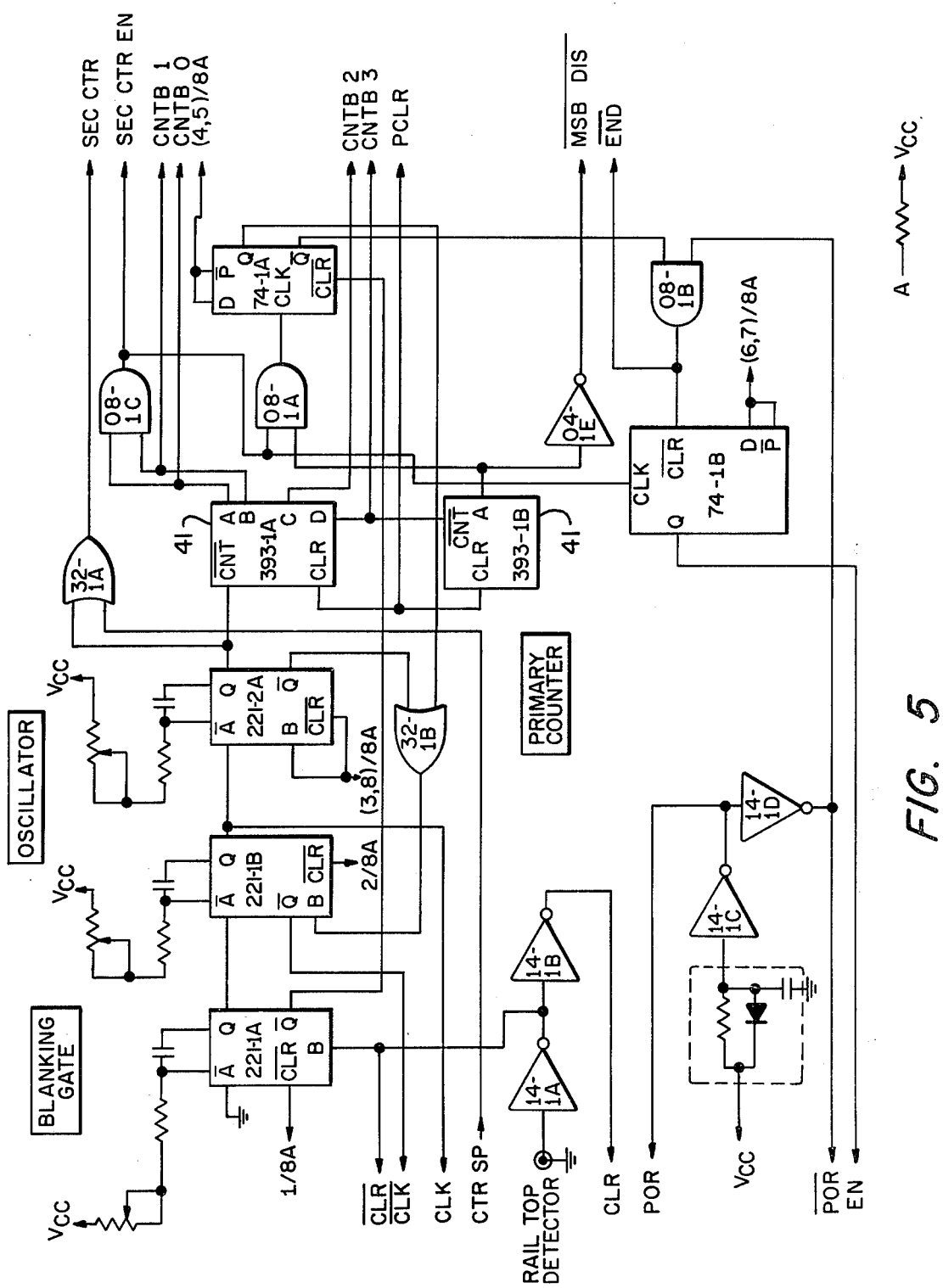
FIG. 5 is the clock detail.

In FIG. 5 shown is the clock which produces the pulses and controls the waves shown in FIG. 4. It also includes a primary counter 41.

Figure 6:
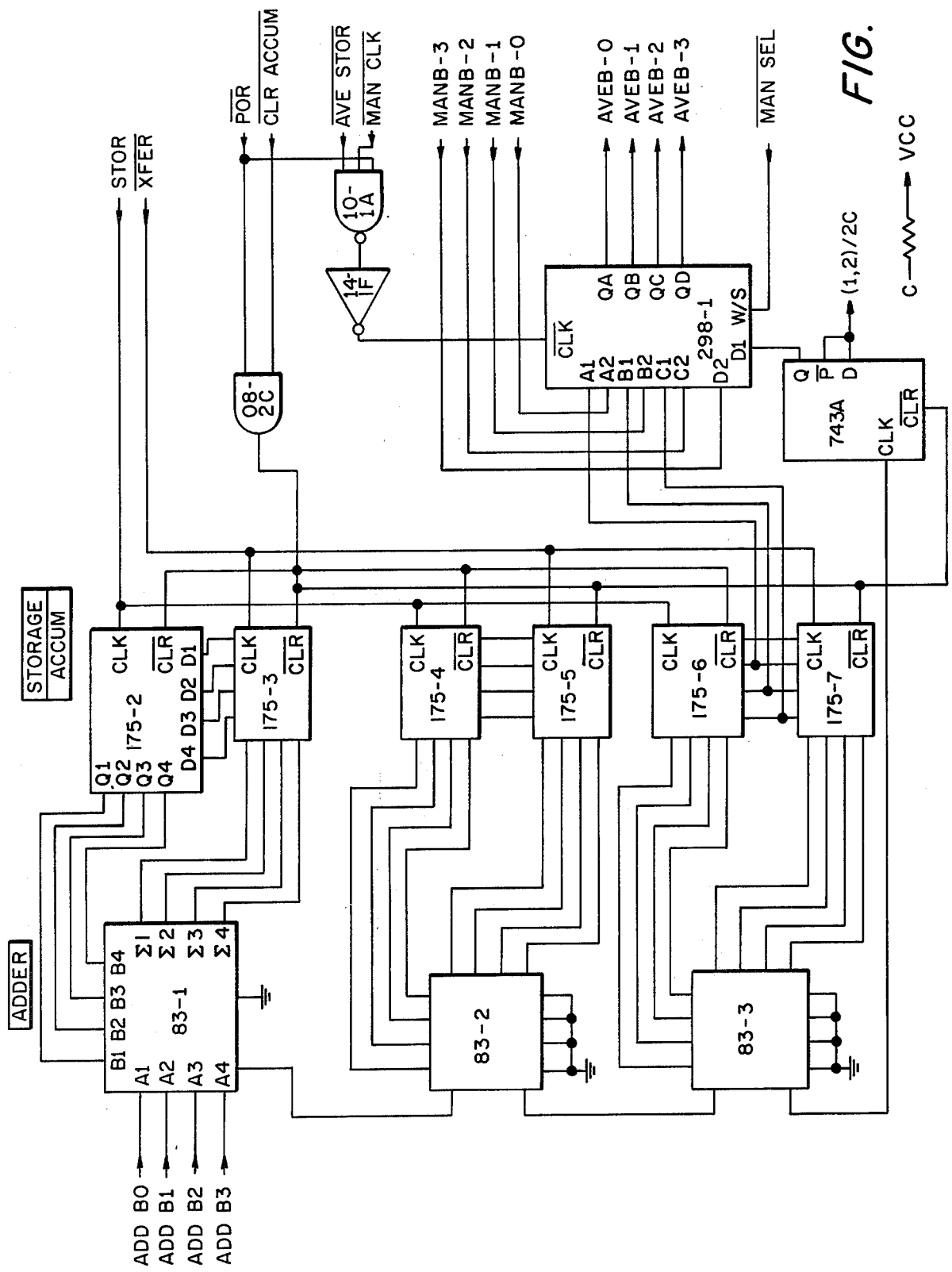
FIG. 6 is the adder.

FIG. 6 is a circuit wherein the individual blocks from the secondary counter are added to produce the signals which can be averaged over a given number of cycles.

Figure 7:
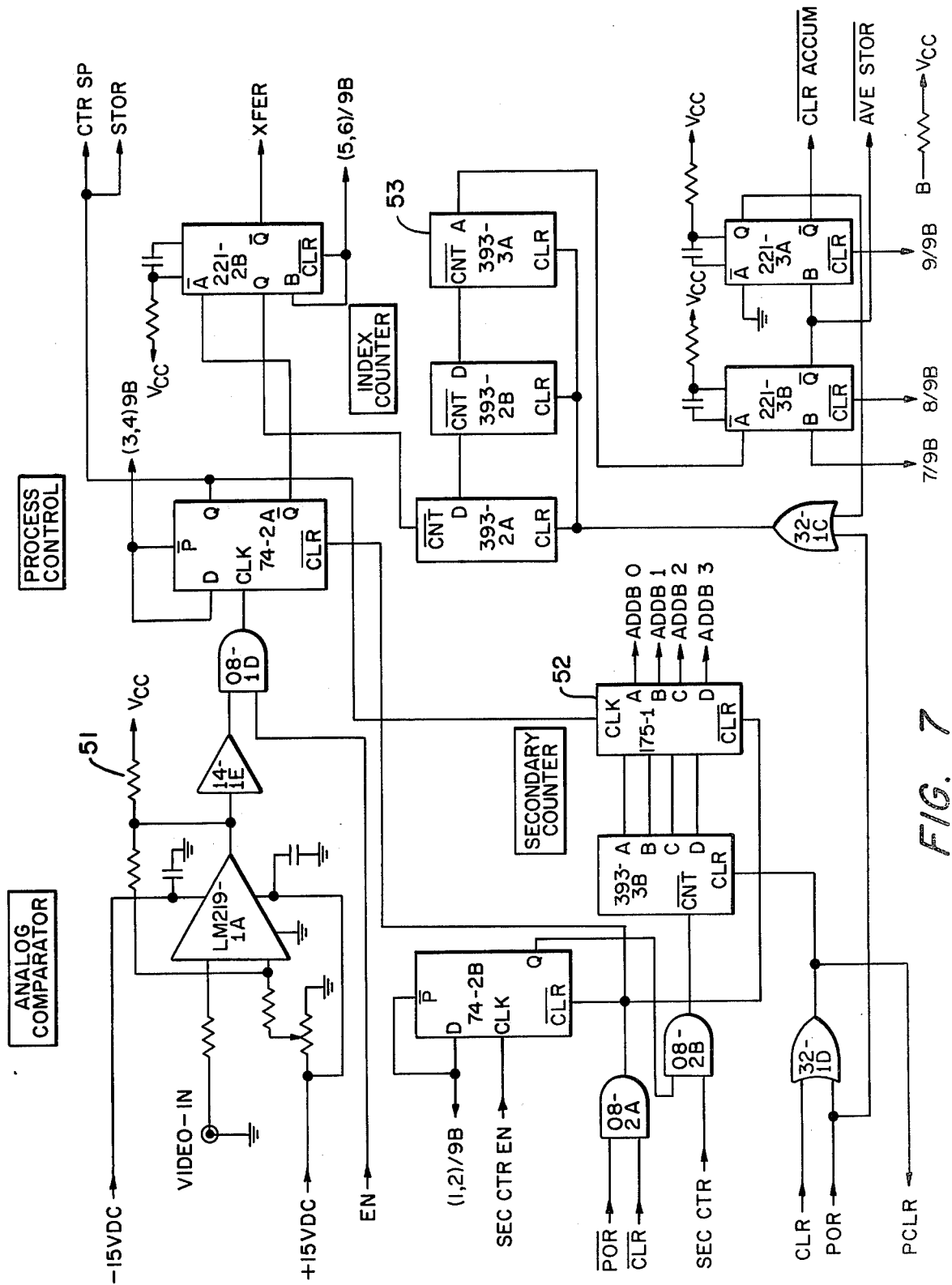
FIG. 7 is the detector.

FIG. 7 shows a circuit in which are contained the base echo digitizer, secondary and index counters.

Figure 8:
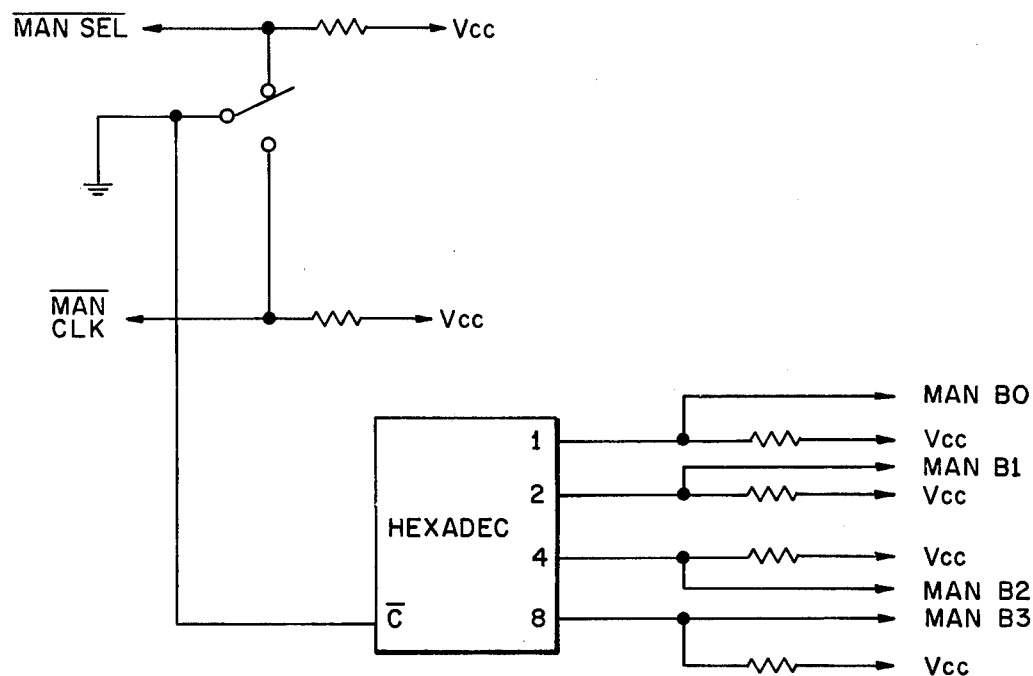
FIG. 8 is the manual control.
Figure 10:
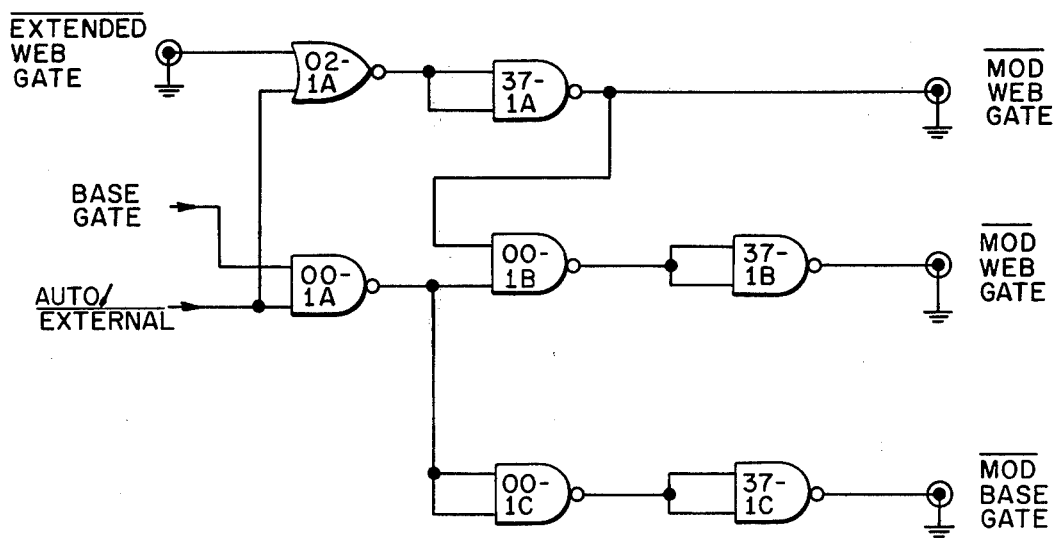
FIG. 10 is the output circuit.

FIG. 8 shows a manual control for the device in order to check its operation and accuracy.

Referring to FIG. 9, shown is a digital gating circuit with its comparator which produces the final base gate to be used in checking the time the echo should be received with a given rail thickness.

A list of the components of the circuits follows:

| | INDUSTRY STANDARD | |
|---|---|---|
| Circuit Designation | Designation | Function |
| 221-1AB, −2AB, 3AB | 74221 | Dual monostable multivibrator |
| 393-1AB, 2AB, 3AB | 74393 | Dual binary counter |
| 74-1AB, 2AB, 3AB | 7474 | Dual D-type flip/flop |
| 83-1, 2, 3 | 7483 | 4-bit adder |
| 175-1, 2, 3, 4, 5, 6, 7 | 74175 | Quad D-type flip/flop |
| 298-1 | 74298 | Quad 2-input multiplexers with storage |
| 85-1 | 7485 | 4-bit magnitude comparator |
| 31-1 A, B, C, D | 7432 | Quad 2-input Or gate |
| 08-1 A,B,C,D, 2 A,B,C,D | 7408 | Quad 2-input And gate |
| 14-1 A,B,C,D,E,F | 7414 | Hex Schmitt trigger inverters |
| 10-1 A,B,C | 7410 | Triple 3-input positive Nand gates |
| 00-1 A,B,C | 7400 | Quad 2-input positive Nand gates |
| 02-1 A,B, | 7402 | Quad 2-input positive Nor gates |
| 37-1 A,B,C | 7437 | Quad 2-input positive Nand buffers |
| LM-219D | LM 219 | High speed dual analog comparator |

-continued

| INDUSTRY STANDARD | | |
|---|---|---|
| Circuit Designation | Designation | Function |
| RLED-1,2,3,4 | | Light-emitting diodes with 10 resistor included |

| POWER CONNECTION | | |
|---|---|---|
| | PIN NO VCC (SVDC) | PIN NO GND (COMMON) |
| 74221 | 16 | 8 |
| 74393 | 14 | 7 |
| 7474 | 14 | 7 |
| 7483 | 5 | 12 |
| 74175 | 16 | 8 |
| 74298 | 16 | 8 |
| 7485 | 16 | 8 |
| 7432 | 14 | 7 |
| 7408 | 14 | 7 |
| 7414 | 14 | 7 |
| 7410 | 14 | 7 |
| 7400 | 14 | 7 |
| 7402 | 14 | 7 |
| 7437 | 14 | 7 |
| | PIN NO +15V | PIN NO COM | PIN NO −15V |
| LM-219D | 11 | 8 | 6 |

1. All fixed resistors ¼ watt unless otherwise specified.
2. all capacities in microfarads unless otherwise specified.
3. Switch S1 single-pole double-throw subminiature toggle.
4. Switch S2 hexadecimal thumbwheel switch with complement.
5. All potentiometers 10-turn wire bound.
6. VCC refers to +5VDC.

Although the invention has been described with reference to specific apparatus, it is to be understood that within the scope of the appended claims the invention may be practiced other than as specifically described herein.

We claim:

1. An automatic base gate positioning circuit in combination with a sonic rail flaw detection system comprising:
    a controllable pulse burst generator for producing a string of uniform pulses spaced a prearranged interval from a sonic input to straddle a range of echoes corresponding to known rail thickness variations;
    first pulse counter means for counting said string of pulses;
    pulse delay means for simultaneously and separately delaying said string of pulses;
    second pulse counter means for counting said delayed string of pulses a preset number of pulses behind said first counter means;
    means for terminating said secondary count in response to selected return echoes;
    means for averaging said terminated secondary count over a preselected number of controllably spaced sonic flaw tests;
    means for comparing said averaged secondary count with said primary count whereby an output signal is triggered when said counts are equal; and
    gate means for receiving said trigger whereby an output gate is positioned to align with displayed echoes from said sonic detection systems.

2. A base gate positioning circuit according to claim 1 wherein said pulse delay means delays said count by three full pulses.

3. A base gate positioning circuit according to claim 1 which further includes means for calibrating the output of said base gate positioning device.

4. A base gate positioning circuit according to claim 3 wherein said averaging means includes an index counter which responds to every complete test cycle of said sonic pulse generator whereby the count is averaged over a controlled series of sonic tests corresponding to a preselected length of rail.

* * * * *